(12) United States Patent
Painchaud et al.

(10) Patent No.: US 8,834,412 B2
(45) Date of Patent: Sep. 16, 2014

(54) DEVICE FOR INJECTING AN IMPLANT

(75) Inventors: Gaetan Painchaud, Francheville (FR); Xavier Donnette, Soleymieu (FR); Pascal Dugand, Estrablin (FR)

(73) Assignee: Rexam Healthcare la Verpilliere (FR)

( * ) Notice: Subject to any disclaimer, the term of this patent is extended or adjusted under 35 U.S.C. 154(b) by 391 days.

(21) Appl. No.: 12/339,628

(22) Filed: Dec. 19, 2008

(65) Prior Publication Data
US 2009/0182267 A1 Jul. 16, 2009

(30) Foreign Application Priority Data
Dec. 21, 2007 (FR) .................................. 07 60289

(51) Int. Cl.
  A61M 31/00 (2006.01)
  A61M 37/00 (2006.01)
  A61M 5/32 (2006.01)
(52) U.S. Cl.
  CPC .................................. *A61M 37/0069* (2013.01)
  USPC .......................................... 604/63; 604/198
(58) Field of Classification Search
  CPC .......... A61M 37/0069; A61M 31/007; A61M 2202/06
  USPC ...................... 604/218, 57–64, 507, 508, 511, 604/514–517
  See application file for complete search history.

(56) References Cited

U.S. PATENT DOCUMENTS

| | | | |
|---|---|---|---|
| 4,105,030 A | 8/1978 | Kercso | |
| 4,597,753 A * | 7/1986 | Turley | 604/61 |
| 5,484,403 A | 1/1996 | Yoakum et al. | |
| 5,695,463 A | 12/1997 | Cherif-Cheikh | |
| 6,102,844 A * | 8/2000 | Ravins et al. | 600/8 |
| 6,270,472 B1 * | 8/2001 | Antaki et al. | 604/61 |
| 6,319,233 B1 * | 11/2001 | Jansen et al. | 604/192 |
| 6,478,768 B1 | 11/2002 | Kneer | |
| 6,530,896 B1 | 3/2003 | Elliott | |
| 6,802,827 B2 * | 10/2004 | Andersson | 604/195 |
| 7,118,552 B2 * | 10/2006 | Shaw et al. | 604/110 |
| 7,798,988 B2 * | 9/2010 | Aubert et al. | 604/57 |
| 2001/0031940 A1 * | 10/2001 | Loos | 604/15 |
| 2004/0199140 A1 * | 10/2004 | Rue et al. | 604/506 |

(Continued)

FOREIGN PATENT DOCUMENTS

| | | |
|---|---|---|
| EP | 0531036 A1 | 3/1993 |
| EP | 0596162 A1 | 5/1994 |

(Continued)

OTHER PUBLICATIONS

French Search Report and Written Opinion, FR 0760289, Aug. 5, 2008, pp. 1-8.

*Primary Examiner* — Quynh-Nhu H Vu
*Assistant Examiner* — Jenna Zhang
(74) *Attorney, Agent, or Firm* — St. Onge Steward Johnston & Reens LLC (57) ABSTRACT

A device for the back-injection of an implant including a holder to allow a user to hold the device, an injection needle, a retainer for retaining the implant before the injection needle, a plunger having a distal part for injecting the implant during withdrawal of the needle, a protective sleeve, capable of adopting an injection position leaving the needle uncovered and a safety position covering the needle again after use of the device, and a spring designed to move the protective sleeve into their safety position, the movement of the spring being controllable by the user.

11 Claims, 3 Drawing Sheets

(56) References Cited

U.S. PATENT DOCUMENTS

| | | | |
|---|---|---|---|
| 2007/0093746 A1* | 4/2007 | Berman et al. | 604/60 |
| 2007/0270759 A1* | 11/2007 | Pessin | 604/192 |
| 2009/0209903 A1* | 8/2009 | Cherif-Cheikh et al. | 604/63 |

FOREIGN PATENT DOCUMENTS

| | | | |
|---|---|---|---|
| EP | 0858813 | A2 | 8/1998 |
| EP | 1323450 | A1 * | 7/2003 |
| EP | 1666085 | A1 | 6/2006 |
| JP | 2003534028 | A | 11/2003 |
| NL | 8901124 | A | 12/1990 |
| WO | 9942148 | A2 | 9/1999 |
| WO | 0038779 | A1 | 7/2000 |
| WO | 0143811 | A1 | 6/2001 |
| WO | WO 2006027447 | A1 * | 3/2006 |
| WO | 2006058745 | A1 | 6/2006 |
| WO | WO 2006058613 | A1 * | 6/2006 |

\* cited by examiner

DEVICE FOR INJECTING AN IMPLANT

CROSS-REFERENCE TO RELATED APPLICATIONS

The present application claims priority of French patent application No. 0760289 filed on Dec. 21, 2007, the content of which is incorporated herein by reference.

FIELD OF THE INVENTION

This invention relates to the technical field of injecting one or more implants into the body of a subject. More specifically, but not exclusively, the invention concerns the intramuscular or sub-cutaneous injection of one (or several) solid or semi solid pharmaceutical components which are designated "implant" in what follows. The subject can be a mammal, particularly a human being. This will be designated as "subject" or "patient" in what follows. This implant is injected periodically, for example each month, into the subject's body about 10 mm (millimeters) below the surface of the subject's skin, this implant then dissolving into the subject's body during the month. In accordance with another possible application, the implant is an electronic chip used to identify a living being.

BACKGROUND OF THE INVENTION

This invention relates to the technical field of injecting one or more implants into the body of a subject. More specifically, but not exclusively, the invention concerns the intramuscular or sub-cutaneous injection of one (or several) solid or semi solid pharmaceutical components which are designated "implant" in what follows. The subject can be a mammal, particularly a human being. This will be designated as "subject" or "patient" in what follows. This implant is injected periodically, for example each month, into the subject's body about 10 mm (millimeters) below the surface of the subject's skin, this implant then dissolving into the subject's body during the month. In accordance with another possible application, the implant is an electronic chip used to identify a living being.

Patent EP 1 323 450 already known in the art teaches a device for injecting tablets of a drug, comprising a hollow needle fixed to a cylinder housing the tablets. The tablets are held in the cylinder before being introduced into the needle and then into the body of the subject. The tablets are maintained in position in the cylinder by flexible fingers which hold the tablets until the operator presses on the device's plunger rod and which then relax to allow the tablets to be introduced into the needle by deflection of the flexible fingers.

A disadvantage of such a device resides in the fact that the deflection of the flexible fingers puts the tablets under stress. The tablets are compressed both by the plunger pressed by the user and by the flexible fingers which exert a certain amount of resistance before giving way. For some implants, exerting stress upon them may be dissatisfactory. Indeed, certain implants are particularly fragile or easy to deform, due to the fact that they contain substances intended to dissolve within the subject's body. The pressure exerted on these implants may therefore damage them. In addition, for a deformable implant, the pressure exerted from above may increase its diameter to such an extent that the implant remains stuck inside the device.

SUMMARY OF THE INVENTION

This invention aims in particular to provide a device which guarantees that implants injected into the subject's body are intact.

This invention therefore concerns a device for injecting an implant comprising:
- a housing for receiving an implant located before an injection needle,
- means for retaining the implant in the receiver housing,
- means for deactivating the retaining means,
- the retaining means being configured so as not to exert any stress on the implant.

A device is thus provided which guarantees that the implant will not be damaged or deformed by a stress. The device comprises deactivating means adapted to prevent the retaining means from damaging the implant when it is introduced into the needle.

It will be understood that "so as not to exert any stress on the implant" consists in not subjecting it to a force which could damage it. The device described above may therefore exert light pressure on the implant but without risk of damaging it. For example, for a PLA or PLGA implant, which are derivatives of lactic and glycolic acids, light pressure of, for example, up to 1 N (Newton) for a very fragile or deformable implant or up to 20 N (Newton) for a more resistant or less deformable implant, can be exerted on the implant without damaging it.

Among the advantages of the invention, it will be noted that the retaining means enable the implant to be held in the receiver housing when the needle has not been introduced into the subject's body and while no pressure has been exerted on the plunger rod. Therefore the device guarantees the user that there is no risk of the implant accidentally falling out of the device before the needle has been inserted into the subject's body. It is particularly important to ensure that the implant is indeed present in the device before injection due to the consequences of an implant not being injected, which can be considerable in medical terms if the user mistakenly believes that the injection has been performed. In addition, it is advantageous for the implant to be retained in the means designed for it before the needle and not in the needle so that the user of the device can ensure when the needle is inserted into the subject's body and preferably even when it is fully inserted that the implant is still in the device. If the implant had been held inside the needle instead of before the needle, once the needle is inserted into the subject's body the user would not be able to verify that the implant is still present in the device since it would no longer be possible to see the needle. This is a significant advantage since an implant that is held insecurely in the device could easily fall out of the device just before injection when the needle is lowered.

The invention may in addition comprise one or more of the following characteristics.

The means for deactivating the retaining means are activated automatically once the needle is at least partially in the insertion position, i.e. inserted into the subject's body. Consequently, the user of the device does not need to perform any specific actions to initiate release of the implant held in the device which facilitates handling the device during injection. In particular, the user does not need to change hands to perform the transfer of the implant into the needle, to inject the implant into the subject's body or to withdraw the needle, and any abrupt movements which could be painful for a patient are therefore avoided.

The deactivating means act directly on the retaining means. In other words, the deactivating means do not act on the retaining means via the implant, thus avoiding any risk of damaging the implant.

The device comprises a plunger and the deactivating means are activated by this plunger, more specifically by the plunger moving into a predetermined position. The retaining means are automatically deactivated when, for example, the user presses the plunger to inject the implant, without any other action being required than to press the plunger.

The retaining means comprise a stop to retain the implant which can be in an activated retaining position before the needle is in the insertion position, i.e. before the needle starts to be inserted into the subject's body, as well as in a deactivated position once the needle is in the insertion position, i.e. once the needle has been at least partially inserted into the subject's body. Preferably, this retaining stop acts in reaction to the weight of the implant to prevent the implant from passing into the needle under the effect of gravity when the device is in the vertical position. This retaining stop can take the form of a stop extending in a transverse direction of the device below the implant, in particular between the implant and the proximal end of the needle.

The retaining stop is supported by a rubber tab.

The retaining means are supported by a retaining element and deactivation comprises firstly interaction between the retaining element and the implant receiver housing and secondly interaction between the retaining element and the plunger.

The deactivation means are adapted to shift the retaining means radially. The retaining stop can move into its deactivated position after a radial shift, generated for instance by a detent built into the implant receiver housing, the detent interacting with the retaining means when the device plunger is displaced.

The device comprises verification means configured so that the implant is visible to the user when it is held by the retaining means, in particular when the needle is in a position not visible to the user, for instance when completely inserted into the subject's body.

This invention also proposes a device for back-injection of an implant. Back-injection consists in injecting the implant while the needle is being withdrawn. The inventors aim to provide a device designed in such a manner that the device user can manually control the withdrawal of the needle from the patient's body. It is desired to avoid automatic withdrawal of the needle, carried out purely under the action of a spring, since automatic withdrawal can be painful to the patient for two reasons in particular: the user injecting the implant may not be used to using a back-injection device and in addition the needles of back-injection devices may be very long.

The invention therefore concerns a device for back-injection of an implant comprising:
  means for a user to hold the device,
  an injection needle,
  needle protection means, with an injection position which leaves the needle uncovered and a safety position covering the needle after use of the device,
  return means for ensuring that the protection means return to their safety position from their injection position,
  the movement of the return means being controllable by the user.

A device is therefore proposed wherein the protective means, usually a protective sleeve, can adopt their safety position to prevent the needle from remaining uncovered after it has been introduced into the patient's body. Preferably this safety position is adopted automatically, for instance by the release of the return means when the device's plunger arrives at the end of its travel, these return means causing a relative movement between the sleeve and needle so that the sleeve can protect the needle. It is proposed that an automatically initiated relative movement takes place between the sleeve and needle without, however, withdrawal of the needle from the patient's body being driven by the return means alone, without the user being able to control the movement of the device. Using this device therefore, the user can control the movement of the return means by at least partially opposing their release, preferably using the holding means so that the user can stop the return means from moving if he wishes or slow down or accelerate them. The holding means generally comprise a grip pressed by the user's fingers, preferably by the user's index and middle finger, fitted at the proximal end of the device. Once the needle has been inserted into the patient's body, withdrawal of the needle can be done at least partially by a backwards movement of the user's fingers so that the distance between the patient's skin and the holding means increases as the needle is withdrawn.

A back-injection device of this type offers the user similar functionality to a liquid injection device with a syringe and automatically released protective sleeve while still providing the technical features required by a device for back-injection of solid or semi-solid implants, notably necessary means for injecting the implant as the needle is withdrawn. It will be noted that implant back-injection has the advantage of not exerting any stress on the implant at the moment it leaves the needle to remain in the patient's body, unlike a standard injection where the product (a liquid drug for instance) is pushed through the patient's skin. In a standard injection, if the implant is fragile it will be broken when it is pushed through the skin. With back-injection, however, the implant does not move through the skin, it fills a cavity left by the needle as it is withdrawn: the implant is transported to the proximal end of the needle while being subjected to as little stress as possible, the needle is then withdrawn from the patient's body leaving the implant in the patient's body at the same depth as when it was at the distal end of the needle. When the needle is withdrawn automatically, under the action of a spring, the user cannot control needle withdrawal manually because of the internal back-injection mechanism which is not accessible from outside the device, which can be disturbing if he is used to using liquid injection devices. If the user is not used to using a back-injection device, his use of the device could be clumsy and therefore painful to the patient. Thanks to the invention, the user can control withdrawal of the needle from the patient's body manually, as with certain liquid drug injection devices. The back-injection device therefore operates in a way familiar to the user. It will be noted that the back-injection device according to the invention preferably ensures automatic back-injection, i.e. that the implant is transferred automatically from the needle into the patient in a single action when then needle is retracted, but that also back-injection can be, at least partially, manual. When the implant is positioned at the distal end of the needle, it can be planned that needle withdrawal, at least at the beginning, is performed manually by the user moving back his fingers. This initial withdrawal of the needle creates a space in the patient's body into which the implant can be introduced without exerting any force upon it, by pressing on the plunger. Then, continuing pressure on the plunger can automatically release the needle protective means and the remainder of the retraction of the needle from the patient's body. The operations of transferring the implant into the patient's body and protecting the needle can therefore be performed simultaneously (automatic back-injection) or successively (manual back-injection).

In addition, the device comprises means for retaining the implant before the injection needle. As explained above, it is particularly advantageous for the implant to be held before the needle and not in the needle so that the user of the device can check, at the moment when the needle is inserted into the subject's body and, preferably, even when it is fully inserted, that the implant is still in the device. Moreover, the implant may be easier to hold before the needle than in the needle. In addition, since the travel range of the implant before leaving the needle is longer when it is held before the needle, there is less risk of the implant leaving the device at the moment when the user is going to insert the needle into the patient's body.

Retention before the needle can be performed as described above using deactivation means or by exerting light pressure on the implant, so as to hold it by friction, for instance with flexible fingers.

The back-injection device may also comprise one or more of the following characteristics.

The device includes a plunger comprised of two separable parts, a distal part and a proximal part, the distal part being intended to position the implant flush with the distal end of the needle.

The device comprises retractable means for connecting the protective means to the holding means. When the device is in the injection position, the protective means are connected to the holding means and when the device is in the safety position, the protective means are disconnected from the holding means. For instance, the retractable connecting means comprise latching means located respectively on the proximal end of the protective means and on a part joined to the holding means.

BRIEF DESCRIPTION OF THE DRAWINGS

The invention will be better understood from the following description, given solely by way of example and by referring to the drawings wherein:

FIG. 2b is a partial longitudinal sectional view of part of the retaining means of FIG. 2a;

FIG. 3b is a longitudinal sectional view along arrow 3b in FIG. 3a;

FIG. 3c is a longitudinal sectional view along arrow 3c in FIG. 3a;

DETAILED DESCRIPTION OF THE INVENTION

Figure 1A:
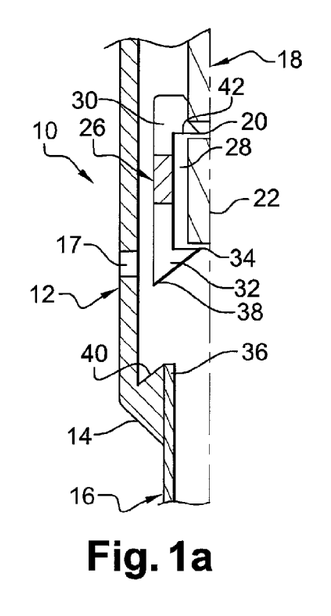
FIG. 1a is a partial longitudinal sectional view of part of a device according to a first embodiment the invention, showing the retaining means in the activated position.
Figure 1B:
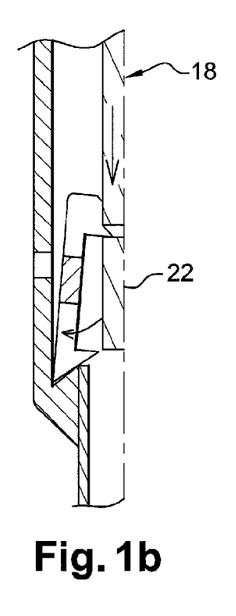
FIG. 1b is a similar view to FIG. 1a, illustrating the retaining means during deactivation.
Figure 1C:
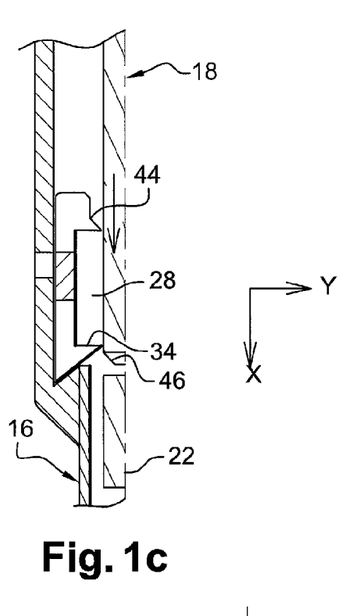
FIG. 1c is a similar view to FIG. 1a, illustrating the retaining means in the deactivated position.

As can be seen in FIGS. 1a to 1c, an injection device 10 comprises a housing 12 for receiving an implant, this housing 12 comprising a distal end 14 to which is fixed, permanently in this example, an injection needle 16 intended to be inserted into the body of a subject. The injection device also comprises a plunger 18, plunger 18 comprising a rod whose proximal end is fitted with a pusher (not shown) and with the distal end fitted with a thrust surface 20. Plunger 18 can be made of several sections as in the third and fourth embodiments.

The device 10 is intended to receive a solid or semi-solid implant 22. In this example, implant 22 is a single block but it could be made of several distinct tablets stacked on top of each other.

According to the example described, the needle 16 is hollow with a diameter of 2 mm and a length of about 40 mm. It is intended to deposit implant 22 at a depth of about 10 mm below the surface of the subject's skin. Implant 22 is particularly fragile or easy to deform and is intended to dissolve in the subject's body, for instance over the course of a month following its injection. It is produced by an extrusion or injection process and comprises a support material made of PLA or PLGA mixed with a drug.

As can be seen, the receiver housing 12 is located just before the injection needle 16. Moreover device 10 comprises visualizing means 17 enabling the presence of implant 22 in the device to be checked. These means 17 are for example a window built into the receiver housing 12, designed so that implant 22 can be seen when it is in the device in a way similar to that shown in FIG. 1a.

In this application, the direction "before" is designated with reference to the direction in which implant 22 is injected. Therefore housing 12 is located before needle 16, i.e. it is located between needle 16 and the proximal end (the end opposite the needle) of device 10.

Device 10 also comprises means 26 for retaining implant 22 in receiver housing 12, the means being able to adopt an activated position shown in FIG. 1a and a deactivated position shown in FIG. 1c. In this example, the retaining means are a perforated retaining element 26 of generally tubular shape. Element 26 is mounted so that it slides within receiver housing 12. Element 26 comprises a tubular housing 28 intended to receive implant 22. This housing 28 is designed so as not to substantially exert any stress on implant 22 when it is situated within element 26, whether the retaining means are in the activated or deactivated position. The retaining means have a proximal end 30 and a distal end 32.

The distal end 32 has a distal retaining stop 34 for securing the implant which can adopt an active retaining position as shown in FIG. 1a and a deactivated retaining position as shown in FIG. 1c. As can be seen on the figures, the retaining stop 34 extends in the transverse direction Y of device 10, this direction Y being perpendicular to the longitudinal direction X of device 10. When in the activated position retaining stop 34 is designed to act against the weight of implant 22 when the device 10 is in the vertical position with needle 16 downwards, as shown on the figures, to prevent implant 22 from entering the needle 16 under the force of gravity when the device is in the position shown in FIG. 1a. As can be seen, this stop 34 is located below implant 22, more specifically between implant 22 and the proximal end 36 of the needle. In its activated position, stop 34 therefore retains implant 22 in the housing 28 before the needle 16. The distal end 32 of retaining means 26 can move between an activated position shown in FIG. 1a and a deactivated position shown in FIG. 1c, by means for example of at least one rubber tab seated on this end 32, this tab supporting stop 34.

Device 10 also comprises means for deactivating the distal retaining means 34. These deactivation means comprise an engagement tooth 38 built into the distal end of retaining element 26, joined onto stop 34, this engagement tooth being intended to interact with a detent 40 formed on the inner distal end of receiver housing 12 so that when the retaining element 26 is in the activated position shown in FIG. 1a, the movement of this element 26 in the direction X generates an interaction between tooth 38 and detent 40 so that the distal retaining stop 34 moves into its deactivated position as shown in FIG. 1c.

The proximal end 30 of the retaining element also comprises a proximal retaining stop 42 to keep the implant in the housing 28 when device 10 is in the vertical position, the needle 16 being uppermost, i.e. in the opposite direction to that depicted in FIG. 1a. As can be seen in FIG. 1a, stop 42 extends in the transverse direction Y of device 10. This stop 42 is supported by one or more rubber tabs supported by the proximal end 30 of retaining element 26. End 30 is also intended to be crossed by plunger 18 and comprises a surface 44 forming a detent intended to interact with a beveled surface 46 at the distal end of plunger 18. The surface 44 forming the detent is primarily intended to form a stop for the distal end of plunger 18 as can be seen in FIG. 1b and then to move radially out of the way by elastic deformation when element 26 is at the end of its travel in the receiver housing 12. The surface 44 and the beveled surface 46 are the means for deactivating retaining stop 42.

Note that retaining means 26 are designed not to exert any stress on implant 22. In particular, if these means 26 exert any pressure on implant 22, this pressure does not exceed a certain force depending on the implant's fragility or strain capability. Depending on the implant, this force does not exceed 1 Newton, or does not exceed 20 Newtons so that the pressure cannot damage or expand the implant 22.

Moreover, element 26 is kept in the position shown in FIG. 1a by means for holding element 26 in the receiver housing 12. Element 26 is held in position for example by light friction between it and receiver housing 12, this friction being overcome when the user of device 10 presses on plunger 18 as can be seen in FIG. 1b, so that element 26 is capable of moving in direction X when plunger 18 is pressed.

The operation of injection device 10 will now be described.

Before inserting the needle 16 into the subject's body, as can be seen in FIG. 1a, the retaining means 26 are in the activated position with the retaining stops 34, 42 holding the implant inside housing 28. As can be seen, implant 22 is held before injection needle 16 and its presence can be checked using the means 17 for verifying the presence of the implant. Moreover, element 26 is held by friction within housing 12 according to the position illustrated in FIG. 1a by the holding means described above.

In FIG. 1a, the needle 16 is positioned in such a way as to be at least partially inserted into the subject's body. In this example, needle 16 in FIG. 1a is considered to be completely inserted into the subject's body, i.e. that it is at the depth with respect to the surface of the subject's skin where it is desired to place the implant 22, for instance the distal extremity of needle 16 is 10 mm from the subject's skin. Note that even if needle 16 is entirely inserted into the skin, the presence of implant 22 can nevertheless be verified using means 17.

Implant 22 is then released by being first introduced into the needle 16 (as can be seen in FIG. 1c) and then into the subject's skin. To perform this injection, the user of the implant device 10 presses on the pusher of plunger 18 which moves it in the longitudinal direction X downwards. When the user presses on plunger 18, the thrust surface 46 of the plunger presses on the thrust surface 44 which moves the retaining element 26 in the X direction, as can be seen in FIG. 1b. The friction exerted by the means for holding element 26 in housing 12 is less than the thrust exerted by the plunger 18 on the thrust surface 44 so that element 26 moves in the X direction when plunger 18 is pressed.

Under the pressure of plunger 18, when element 26 reaches the end of its travel within receiver housing 12 (shown in FIG. 1b), the engagement tooth 38 and detent 40 interlock, radially moving the rubber tabs on the distal end 32 and in particular the retaining stop 34. Since this retaining stop 34 is moved away from the central axis of the injection device 10, it is in the deactivated position so that it no longer retains implant 22 in housing 28. Moreover, since retaining element 26 has reached the end of its travel in the receiver housing 12, further pressure on the plunger 18 by the user causes the proximal end 30 of retaining element 26 to deform. More specifically, the surface 46 of the plunger acts on the detent 44 which deforms, allowing plunger 18 to cross through retaining element 26. The plunger 18 can then push implant 22 into needle 16 as can be seen in FIG. 1c. In this position, implant 22 is in the needle and can then be injected into the subject's body.

As can be seen, the various deactivation means, firstly the tooth 38 and detent 40 and secondly the detent 44 and thrust surface 46 are initiated automatically once the needle 16 has been inserted into the subject's body. These deactivation means are operated by plunger 18, more precisely by the movement of the plunger from an initial position shown in FIG. 1a to a final position shown in FIG. 1c.

Moreover, the deactivation means 38, 40; 44, 46 act directly on the retaining means 26, more specifically by interaction between on one hand the receiver housing 12 and the retaining element 26 and on the other between plunger 18 and retaining element 26. Consequently, these deactivation means do not act directly on implant 22 so that no stress is exerted on the implant to deactivate the retaining means.

Note that the invention is not limited to the previously described embodiments.

Figure 2A:
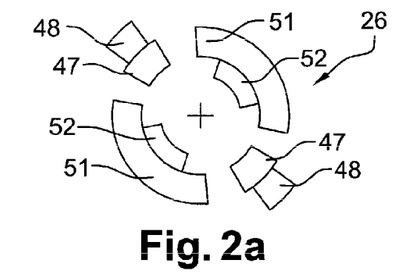
FIG. 2a is a top view of the retaining means in a device according to a second embodiment of the invention.
Figure 2B:
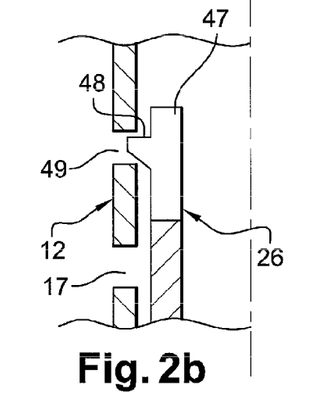
Figure 2C:
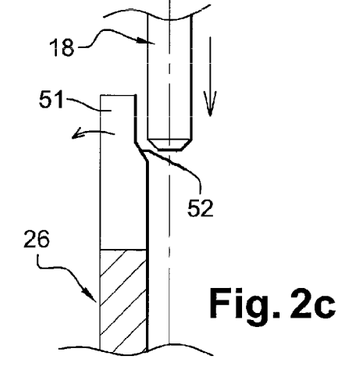
FIG. 2c is a partial longitudinal sectional view of part of the retaining means of FIG. 2a, the sectional view being perpendicular to the sectional view of FIG. 2b.

In the embodiment in FIGS. 1a to 1c, element 26 is maintained in receiver housing 12 by friction between element 26 and housing 12. Another advantageous way of keeping element 26 in housing 12 is shown in FIGS. 2a to 2c. As can be seen in FIG. 2a, the retaining means 26 in this embodiment comprise four rubber tabs on its proximal end 30. Two of these diametrically opposed rubber tabs, referenced 47, have lugs 48 on their outer surface, these lugs being intended to engage with a slot 49 made in the receiver housing 12, as can be seen in FIG. 2b. These means 48, 49 constitute an upper stop for positioning element 26 intended to ensure it is maintained in an initial position similar to that in FIG. 1a with a light engagement. This engagement is released when plunger 18 moves down so that element 26 is moved in accordance with FIG. 1b. Moreover, two other diametrically opposed tabs 51 are located on the proximal end of element 26. These tabs 51 have interior lugs 52 intended to form detents similar to detent 44 as can be seen in FIG. 2c. This embodiment ensures extremely reliable positioning of element 26 in its initial position shown in FIG. 1a.

Moreover, the retaining element in these examples is an element 26 of generally tubular shape whose distal end 32 and proximal end 30 comprise rubber tabs. The retaining means can take numerous other shapes. According to another example, this retaining element 26 could have a generally tapered shape, the diameter of its distal end 32 being greater than the diameter of its proximal end 30 to ensure more reliable interaction between elements 38, 40, 44, 46. Moreover, this element 26 is not necessarily a part separate from the other parts of the implant device. The retaining means could be made using one or more parts of the injection device 10 that have a function other than that of retaining implant 22.

Moreover, the injection device described above can be a back-injection device as will be described below.

An injection device 60 according to a third, fourth and fifth embodiment of the invention will now be described, in reference to FIGS. 3a to 5.

Figure 3A:
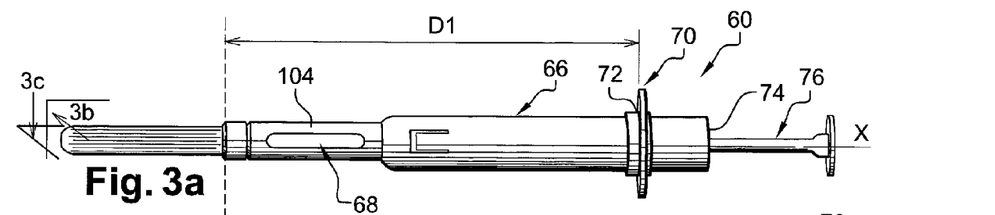
FIG. 3a is a side view of an injection device according to a third embodiment of the invention, the device being represented in the injection position.
Figure 3B:
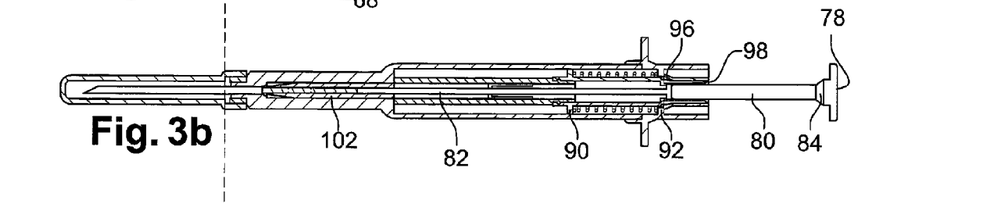
Figure 3C:
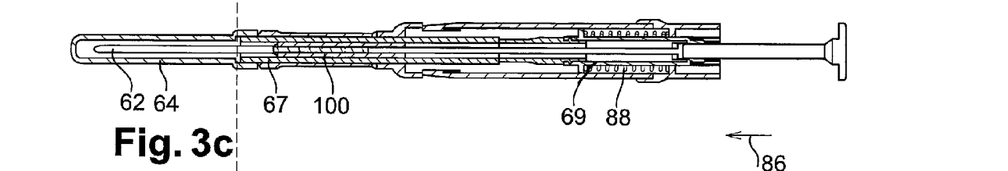
Figure 3D:
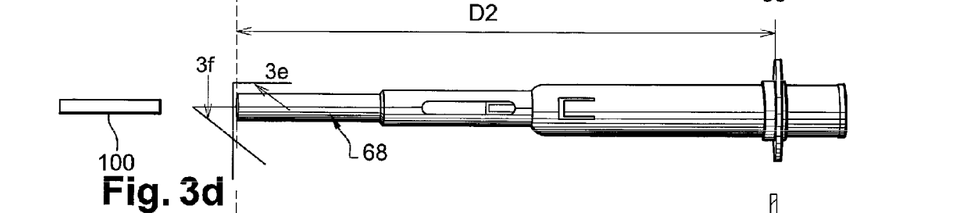
FIGS. 3d, 3e and 3f are respectively similar views to views 3a, 3b and 3c, the device being in its safety position.
Figure 3E:
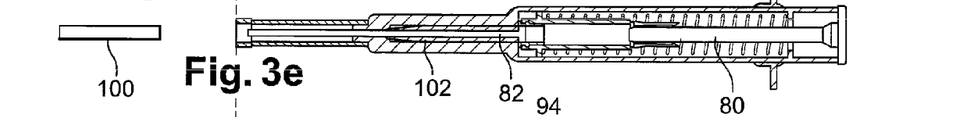
Figure 3F:
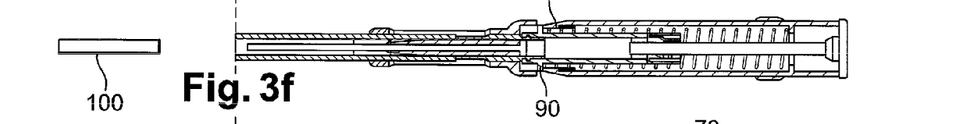

As can be seen in FIGS. 3a to 3f, according to a third embodiment the device 60 comprises an injection needle 62 which before device 60 starts to be used is covered by a protective cap 64. Device 60 also comprises an intermediate housing 66 and protective means 68 referred to in the remainder of the document as "protective sleeve 68", intended to cover the needle again after using the device, as can be seen in FIGS. 3d to 3f. In this embodiment, the intermediate housing 66 is external and the sleeve 68 positioned within intermediate housing 66, co-axially with the longitudinal X axis of the device.

In this embodiment, sleeve 68 is made of two parts, i.e. a distal part 67 which protects the needle when the device is in the safety position and a proximal part 69, fastened to the distal part 67, which holds the sleeve in the injection position and also holds the sleeve in the safety position.

The intermediate housing 66 includes means 70 for holding the device. The holding means 70 comprise a grip 72 for supporting the user's fingers, in particular the user's index and middle finger. In this example, the holding means 70 comprise a rotating flange projecting out from the intermediate housing 66 next to its proximal end 74. The device 60 also comprises a plunger 76. As can be seen in particular in FIGS. 3b and 3e, plunger 76 comprises a pusher 78, to be pressed by the user's thumb, a proximal part 80 and a distal part 82 which can be separated from proximal part 80. Plunger 76 also comprises means 84 for releasing the return means as described below, these means 84 comprising a funnel shape between the proximal part 80 and pusher 78 intended to form an impulse surface when the plunger is moved in the direction indicated by arrow 86.

The device 60 also comprises return means 88, situated between the intermediate housing 66 and the sleeve 68, which are compressed when device 60 is in the injection position and which can adopt an extended or rest position when the device is in the safety position as shown in FIGS. 3d to 3f. Means 88 are a compression spring.

As shown in FIG. 3b, means 88 are maintained in a compressed state, in the injection position, by a distal stop 90 built into sleeve 68 and by a proximal stop 92 built into intermediate housing 66. As shown in FIG. 3f, the distal stop 90 of the sleeve can move in translation into a safety position. In this embodiment, stop 90 also acts to keep sleeve 68 in the safety position by engaging with means such as rubber tabs 94 that can move radially, supported by intermediate housing 66.

Sleeve 68 is held in the injection position by retractable lugs 96 built into its proximal part 69, more specifically near the proximal end of this proximal part 69. The proximal part 69 also comprises means 98 for releasing return means 88 intended to act in conjunction with means 84 of plunger 76.

As shown in FIGS. 3a to 3c, sleeve 68 and intermediate housing 66 form together at their distal end a housing for receiving one or more implants 100, located before needle 62, intended to be injected into the body of a patient. Device 60 also comprises means 102 for retaining implant 100 in the receiver housing. In the example of FIGS. 3a to 3f, the retaining means 102 fulfill their retaining function by means of flexible fingers exerting light pressure on implant 100. Nevertheless, these retaining means 102 can be replaced by retaining means such as those described above, for example by retaining means 26 which can be deactivated by deactivation means so as to exert virtually no stress upon implant 100.

The intermediate housing 66 also comprises verification means 104, in this example comprised of a window built into housing 66, enabling the user to see whether implant 100 is held effectively by retaining means 102.

The operation of the device shown on FIGS. 3a to 3f will now be described.

Before using back-injection device 60, implant 100 is present in the device, its presence being checked with means 104. Injection starts by removing protective cap 64 to leave needle 62 uncovered so that the user of the device can insert it into the body of the patient into whom it is desired to inject implant 100. The user holds device 60 between his index and middle finger, these two fingers pressing against holding means 72 with the user's thumb ready to push the pusher 78 in the direction of arrow 86. Note that the needle is completely uncovered before being introduced into the patient's body so that the user can see exactly what he is doing and can manually control the insertion of the needle as with a liquid injection device. Once the needle has been completely introduced into the patient's body, whose skin is represented by the dotted line 106, the user pushes plunger 76 by pressing on pusher 78. The movement of pusher 78 causes proximal part 80 of the plunger's distal part 82 to move, causing implant 100 to move into needle 62. Once implant 100 is positioned flush with the distal end of needle 62, plunger 76 reaches a position in which means 84 can engage with means 98. More specifically, impulse surface 84 of plunger 76 causes socket 98 in sleeve 68 to move radially aside, this movement causing tabs 96 to retract and return means 88 to be released. This retraction causes tabs 96 to pass beyond retaining projection 92 of the intermediate housing 66 in the direction of arrow 86 so that the retaining stop 90 of sleeve 68 moves in the direction of arrow 86 under the force of return means 88. This displacement moves sleeve 68 in direction 86 which causes plunger part 82, which has been previously fastened to sleeve 68 by friction or click tabs, to move into the needle to keep the implants in place and causes the sleeve 68 to adopt the safety position shown in FIGS. 3d to 3f so that sleeve 68 can cover needle 62 again as it is withdrawn from the patient's body. Once the needle has been completely withdrawn, it is covered completely by sleeve 68 and stops 90 engage with means 94 in housing 66 to keep the device in the safety position. Since part 82 of the plunger pushes automatically on the implant to keep it in the patient's body as the sleeve is released, the term automatic back-injection is used.

Note that, as an alternative, back-injection can be performed manually. In this case, plunger 76 is in a single part which cannot be attached to sleeve 68 and implant injection takes place before tabs 96 are retracted. At the moment when implant 100 is at the distal end of needle 62, the user can slightly withdraw device 60 which starts to remove the needle and leaves a space in the patient's body to introduce implant 100 without any stress. After this slight withdrawal, the user can press again on pusher 78, which enables plunger 76 (not fastened to the sleeve) to push implant 100 into the patient's body. Then, further pressure on pusher 78 causes tabs 96 to retract, automatically releasing protective means 68.

As can be seen from the figures, the distance between the holding means 70 and the patient's skin 106 has been increased from value $D_1$ when the device is in the injection position to value $D_2$ when the device is in the safety position. Device 60 therefore enables implant 100 to be back-injected, i.e. implant 100 is injected or more precisely remains in position in the patient's body at the moment when the needle 62 is withdrawn from the patient's body. In addition to back-injection, the invention proposes automatic protection of the needle by the sleeve 68 as it is withdrawn, the needle not being left uncovered while allowing the user to control needle withdrawal manually with means 70. To withdraw needle 62 from the patient's skin 106, the user's fingers move backwards. If the user does not control his fingers, they are moved by the movement of return means 88 which initiate release of sleeve 68 from within intermediary housing 66. In this case, needle withdrawal occurs automatically without manual control by the user. Nevertheless, the user can control needle withdrawal manually by controlling the movement of means 88 with means 70. The user can for instance slow down or stop the movement of means 88 by exerting a force on holding means 70 against the force exerted by return means 88.

The back-injection device 60 illustrated in FIGS. 4a to 4f has a different structure to the device of FIGS. 3a to 3f but similar operation.

Figure 4A:
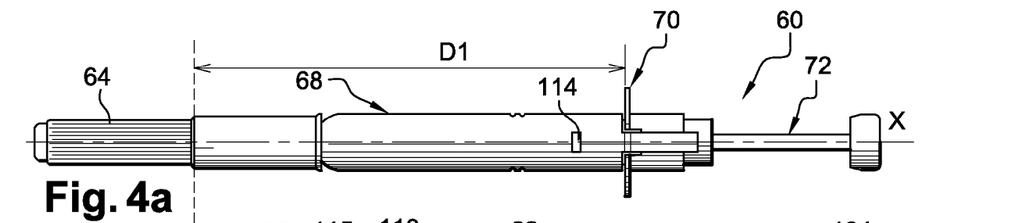
FIGS. 4a to 4f are respectively similar views to FIGS. 3a to 3f of an injection device according to a fourth embodiment of the invention.
Figure 4B:
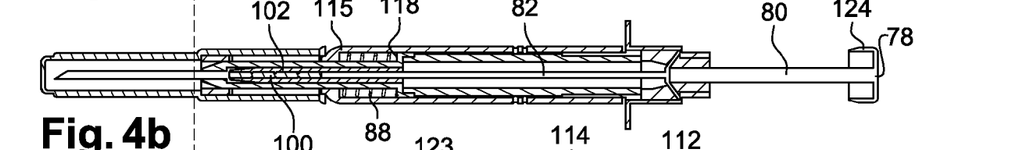
Figure 4C:
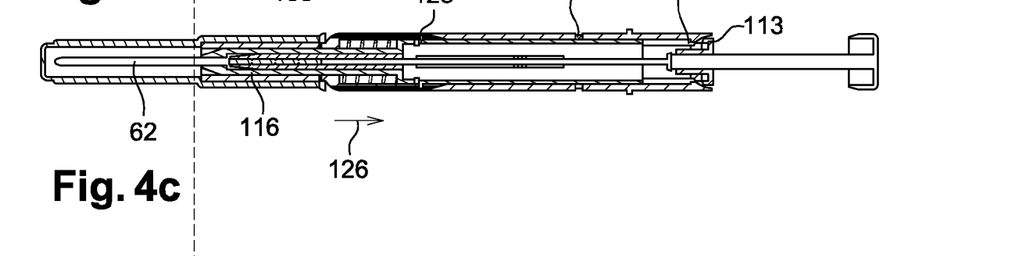

In this embodiment, the sleeve 68 is on the outside and the intermediate housing 66 moves inside sleeve 68 co-axially with respect to axis X.

In this embodiment, sleeve 68 has retractable means 110 at its proximal end, comprised in this example of two rubber tabs 110, each with retractable lugs 112 intended to engage with intermediate housing 66. The retractable lugs 110 also comprise detents 113 intended to engage with plunger 72. Sleeve 68 also comprises means 114 for keeping the sleeve in the safety position, these means 114 being intended in the example to engage with intermediate housing 66.

In addition, sleeve 68 comprises a stop 115 intended to press on return means 88. The intermediate housing 66 comprises a body 116 for receiving the implant 100, the implant being held in position by retaining means 102. In addition, the intermediate housing 66 comprises a stop 118 intended to press on the proximal end of return means 88. In this embodiment, the intermediate housing 66 is made of two parts, a proximal part 120 supporting holding means 70 fastened to a distal part 122, comprising the body for receiving the implant 100. The intermediate housing 66 is fitted with means 123 for keeping sleeve 68 in the safety position, in this case tabs 123 intended to engage with slots 114.

In this embodiment, the pusher 78 of the plunger 72 incorporates means 124 for releasing securing means 112, through the shape of the cap on pusher 78.

The operation of device 60 shown on FIGS. 4a to 4f is similar to that of the device shown on FIGS. 3a to 3f, the main steps being described below.

Figures 4D, 4E, 4F:
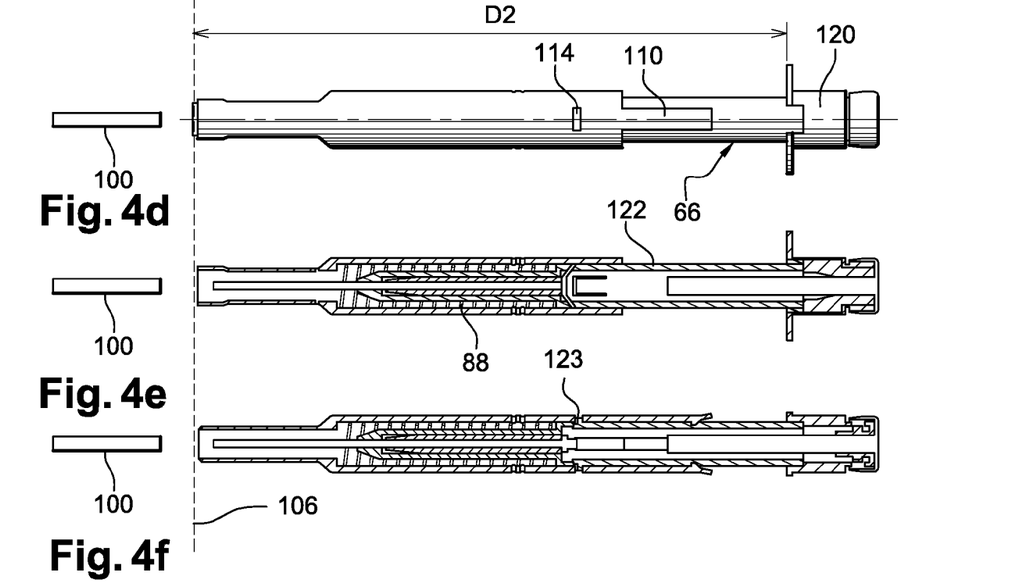

The user first removes the protective cap 64 and then inserts the needle 62 into the patient's body. The user then pushes on pusher 78 which moves rods 80 and 82 of plunger 72 and therefore the implant 100 which is introduced into the distal end of the needle 62. When plunger 72 reaches the end of its travel, release means 124 engage with the rubber detent 113 moving the rubber tabs 110 radially out of the way and retracting lugs 112. Once lugs 112 have retracted, the return means 88 are released and can extend in the direction indicated by arrow 126. This release of return means 88 causes intermediate housing 66 to move in the direction of arrow 126 and thus to protect needle 62 by sleeve 68 as shown in FIGS. 4d to 4f. The device is then held in the safety position by the interaction of means 114 and 123.

In the same way as for the third embodiment, it can be seen that the user can control withdrawal of the needle from the patient's skin 106 manually.

Figure 5:
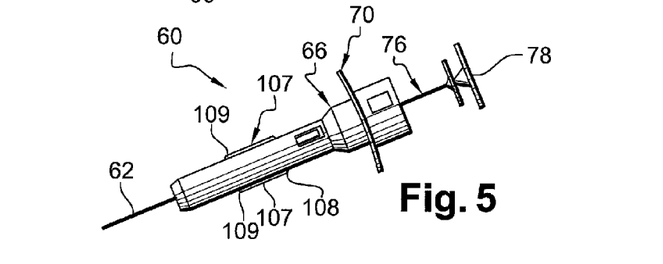
FIG. 5 is a view of a device according to a fifth embodiment of the invention.

The embodiment of FIG. 5 is relatively similar to that of FIGS. 3a to 3f. Nevertheless, in addition to holding means 70 at the proximal end of intermediate housing 66, the device 60 comprises means 107 for guiding the distal holding of the device, distal holding being intended to facilitate insertion of the needle into the patient's body. These means 107 are fitted to housing 66 near its distal end. They can comprise a visual indicator, a protuberance (as shown in FIG. 5) or a roughened surface. They are intended to indicate a distal zone that the user can use to perform the injection.

Obviously, such guide means 107 can be implemented on all the other embodiments. In the case of the embodiment of FIG. 4, means 107 could be installed on the sleeve 68.

A few remarks on the operation of the device of FIG. 5 which are equally applicable to the other embodiments will now be made. Before starting to inject the patient, device 60 is in the configuration of FIG. 5. To introduce the needle 62 into the skin, the user holds device 60 by its distal part, preferably by holding the guide area 107 between the fingers of his right hand if he is right-handed. It may be more practical for the user to introduce the needle while holding device 60 in this zone 107, since device 60 may be relatively long, for example a length of 200 mm between the end of needle 62 and pusher 78. More precisely, the user holds the proximal end 108 of the guide zone 107 with his right hand. With his other hand, the left hand, the user can pinch the patient's body to create a hard surface for introducing the needle. Once the needle has been completely inserted into the patient's body, the user can stop pinching the patient's body and with his freed left hand take hold of the distal end 109 of zone 107, freeing his right hand which lets go of end 108 and can then grip the holding means 70 to activate plunger 76 and proceed onto the steps of injection and needle withdrawal. In the embodiment of FIG. 5, plunger 76 is made of a single part and back-injection is preferably manual.

Note that the embodiments of the back-injection device 60 can take forms other than those described. In particular, the embodiments can be combined with any of the other embodiments.

Note that the devices of the third, fourth and fifth embodiments (FIGS. 3a to 5) are devices for back-injection of an implant, preferably automatic back-injection but also being able to perform manual back-injection as has been described. A device provided with automatically released protective means 68 is therefore proposed, avoiding contamination by the needle and ensuring manual or automatic back-injection, guaranteeing that the implant is injected without experiencing any stress. Whether back-injection is manual or automatic, the invention proposes to control manually the movement of protective means 68 using holding means 70. For manual back-injection, the user carries out the implant injection himself, by withdrawing the needle from inside the patient's body and exerting pressure on the plunger before the automatic release of the protective means. For automatic back-injection, the operator does not have to worry about injecting the implant, this being performed during the release of the protective means, since the sleeve and distal part 82 of the plunger are fastened together beforehand, so that the release of the sleeve causes part 82 to act and transfer the implants towards the skin when the needle is withdrawn from the body.

Similar operation can be envisaged for an injection device other than a back-injection device.

What is claimed is:
1. A device for back-injection of an implant comprising:
a grip for a user to hold the device;
an injection needle;
a retaining element for retaining the implant proximal to the injection needle;
a plunger including a distal part for injecting the implant during withdrawal of the injection needle, the plunger comprising two separable parts, the distal part and a proximal part, the distal part for positioning the implant flush with the distal end of the injection needle;

a protective sleeve adopting an injection position leaving the injection needle uncovered prior to use of the device and a safety position covering the injection needle after use of the device; and a compressible spring moving the protective sleeve automatically into the safety position, the movement of the compressible spring being controllable by the user at least partially opposing the release of the compressible spring;

wherein the distal part of the plunger is fastenable to the protective sleeve, and the distal part separates from the proximal part and the compressible spring moves the distal part into the injection needle to keep the implant in place while the protective sleeve moves together with the distal part of the plunger into safety position by the compressible spring.

2. The device according to claim 1, comprising retractable lugs for securing the protective sleeve to the grip.

3. The device according to claim 1, wherein the retaining element performs a retaining function with flexible fingers exerting light pressure on the implant.

4. The device according to claim 1 comprising:

a housing for receiving the implant located proximal to the injection needle, wherein the retaining element also retains the implant in the housing, a deactivating element for deactivating the retaining element, the retaining element being configured so as not to exert any stress on the implant.

5. The device according to claim 4, wherein the retaining element is operated by the plunger, more precisely by the movement of plunger into a pre-determined position.

6. The device according to claim 4, wherein the retaining element comprises a stop, which can adopt an activated retaining position prior to the injection needle being in the insertion position and a deactivated position once the injection needle is in the injection position.

7. The device according to claim 6, wherein the retaining is supported by a rubber tab.

8. The device according to claim 4, wherein deactivation comprises, firstly, interaction between the retaining element and the housing and, secondly, interaction between the retaining element and the plunger.

9. The device according to claim 4, wherein deactivating element is configured to shift the retaining element radially.

10. The device according to claim 4, comprising a verification window configured so that the implant is visible to a user when the implant is held by the retaining element, notably when the injection needle is in a position not visible to the user.

11. The device according to claim 1, wherein the grip is configured to receive a force at least partially opposing the release of the compressible spring.

* * * * *